US006294177B1

(12) United States Patent
Fattom

(10) Patent No.: US 6,294,177 B1
(45) Date of Patent: *Sep. 25, 2001

(54) STAPHYLOCOCCUS AUREUS ANTIGEN-CONTAINING WHOLE CELL VACCINE

(75) Inventor: Ali Ibrahim Fattom, Rockville, MD (US)

(73) Assignee: NABI, Rockville, MD (US)

(*) Notice: Subject to any disclaimer, the term of this patent is extended or adjusted under 35 U.S.C. 154(b) by 0 days.

This patent is subject to a terminal disclaimer.

(21) Appl. No.: 09/307,775

(22) Filed: May 10, 1999

Related U.S. Application Data

(63) Continuation of application No. 09/102,214, filed on Jun. 22, 1998, now Pat. No. 6,194,161, which is a continuation-in-part of application No. 08/712,438, filed on Sep. 11, 1996, now Pat. No. 5,770,208.

(51) Int. Cl.[7] .................. A61K 39/085; A61K 39/395; A61K 39/40
(52) U.S. Cl. .................. 424/243.1; 424/243.1; 424/137.1; 424/165.1
(58) Field of Search .................. 424/184.1, 197.11, 424/203.1, 234.1, 243.1, 137.1, 165.1

(56) References Cited

U.S. PATENT DOCUMENTS

| | | | |
|---|---|---|---|
| 4,748,020 | 5/1988 | Maisen-Ponickau | 424/92 |
| 5,032,522 | 7/1991 | Watson | 435/252.1 |
| 5,770,208 | * | 6/1998 | Fattom et al. | 424/197.1 |

FOREIGN PATENT DOCUMENTS

| | | |
|---|---|---|
| WO 98/10788 | 3/1998 | (WO). |
| WO 00/56357 | 9/2000 | (WO). |

OTHER PUBLICATIONS

Karakawa et al.; "Method for the Serological Typing of the Capsular Polysaccharides of *Staphylococcus aureus*"; Journal of Clinical Microbiology; vol. 22, No. 3; Sep. 1985; pp. 445–447.
Fattom et al.; "A *Staphylococcus aureus* Capsular Polysaccharide (CP) Vaccine and CP–Specific Antibodies Protect Mice Against Bacterial Challenge"; Infection and Immunity; vol. 64, No. 5; May 1996; pp. 1659–1665.
Fattom et al.; "Laboratory and Clinical Evaluation of Conjugate Vaccines Composed of *Staphylococcus aureus* Type 5 and Type 8 Capsular Polysaccharides Bound To *Pseudomonas aeruginoas* Recombinant Exoprotein A"; Infection and Immunity; vol. 61; Mar. 1993.
Waldmann; "Monoclonal Antibodies in Diagnosis and Therapy"; Science; vol. 252; Jun. 21, 1991; pp. 1657–1662.
Roitt et al.; "Immunotherapy" Immunology; 4th Edition; 1996; pp. 20.0–20.10.

Anthony et al.; Gram Positive Bacteria: An Overview and Summary of Session Reviews of Infectious Diseases; vol. 10, No. 2; 1988; pp. 5345–5350.
Foster; "Potential for Vaccination Against Infections Caused by *Staphylococcus aureus*"; Vaccine; vol. 9; pp. 221–227, (No Date).
Fattom; "Synthesis and Immunologic Properties in Mice of Vaccines Composed of *Staphylococcus aureus* Type 5 and Type 8 Capsular Polysaccharides to *Pseudomonas aeruginosa* Exotoxin A"; Infection and Immunity; vol. 58, No. 7; 1990; pp. 2367–2374.
Fournier; Purification and Characterization of *Staphylococcus aureus* Type 8 Capsular Polysacchide; Infection and Immunity; vol. 45, No. 1; 1984; pp. 87–93.
Moreau; "Structure of the Type 5 Capsular Polysaccharide of *Staphylococcus aureus*"; Carbohydrate Research; vol. 201; 1990; pp. 285–297.
Davison et al.; "Teichoic Acids in the walls of Staphylococci: Serological Investigations on Teichoic Acids from the Walls of Staphylococci"; Nature; vol. 202; May 30, 1964; pp. 872–874.
Endl; "Chemical Composition and Structure of Cell Wall Teichoic Acids of Staphylococci" Archives of Microbiology; vol. 135; 1983; pp. 215–223.
Rajbhandary et al.; "The Intracellular Teichoic Acid from *Staphylococcus aureus* H"; Biochem Journal; vol. 87; 1963; pp. 429–435.
Fattom et al., "Antigenic Determinants of *Staphylococcus aureus* Type 5 and Type 8 Capsular Polysaccharide Vaccines" Infection and Immunity, Oct. 1998, p. 4588–4592, Pub. American Society for Microbiology.
Naso et al., "Polysaccharide Conjugate Vaccines for the Prevention of Gram–Positive Bacterial Infections" Novel Strategies in Design and Production of Vaccines pp 133–140, 1996, Pub. Plenum Press.
C. N. O'Brian et al., "Production of Antibodies to *Staphylococcus aureus* Serotypes 5, 8, and 336 Using Poly (DL–Lactide–co–Glycolide) Microspheres" J. of Dairy Science, vol. 83, No. 8, pp. 1758–1766, 2000.

* cited by examiner

Primary Examiner—Mary E. Mosher
Assistant Examiner—Shanon A. Foley
(74) Attorney, Agent, or Firm—Foley & Lardner

(57) ABSTRACT

A negatively-charged *S. aureus* antigen contains β-hexosamine as a major carbohydrate component. *S. aureus* strains that carry the antigen account for nearly all of the clinically significant strains of *S. aureus* that are not Type 5 or Type 8 strains. The antigen can be used in combination with *S. aureus* Type 5 polysaccharide antigen and *S. aureus* Type 8 polysaccharide antigen to provide nearly 100% coverage of *S. aureus* infection. The antigen and antibodies to the antigen are useful in kits and assays for diagnosing *S. aureus* infection. A whole cell vaccine of cells that contain the antigen is particularly useful in the treatment of mastitis.

26 Claims, 6 Drawing Sheets

Type 8

Type 5

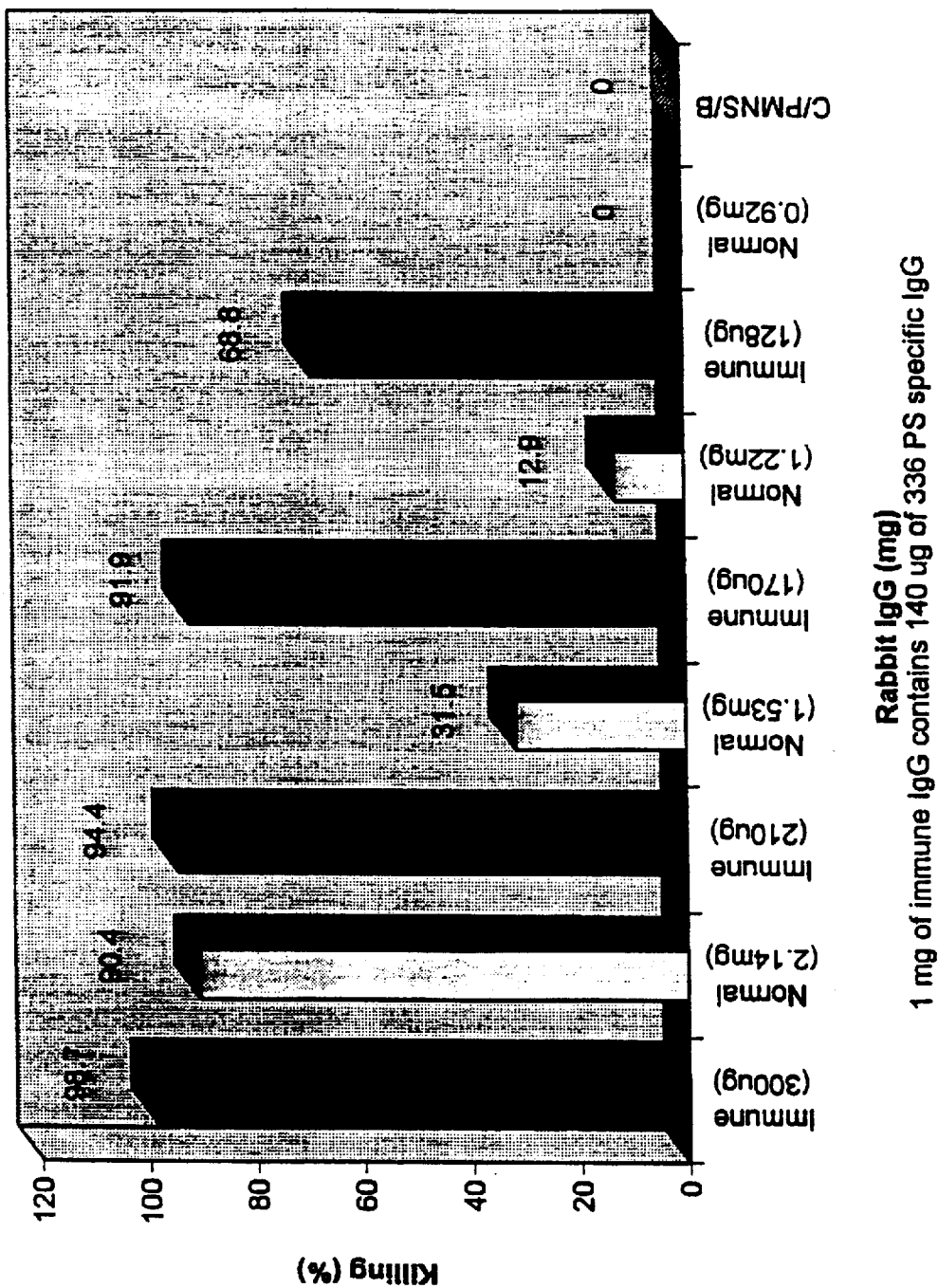

Figure 3  Efficacy of 336 whole cell antibodies in whole blood opsonophagocytic assay
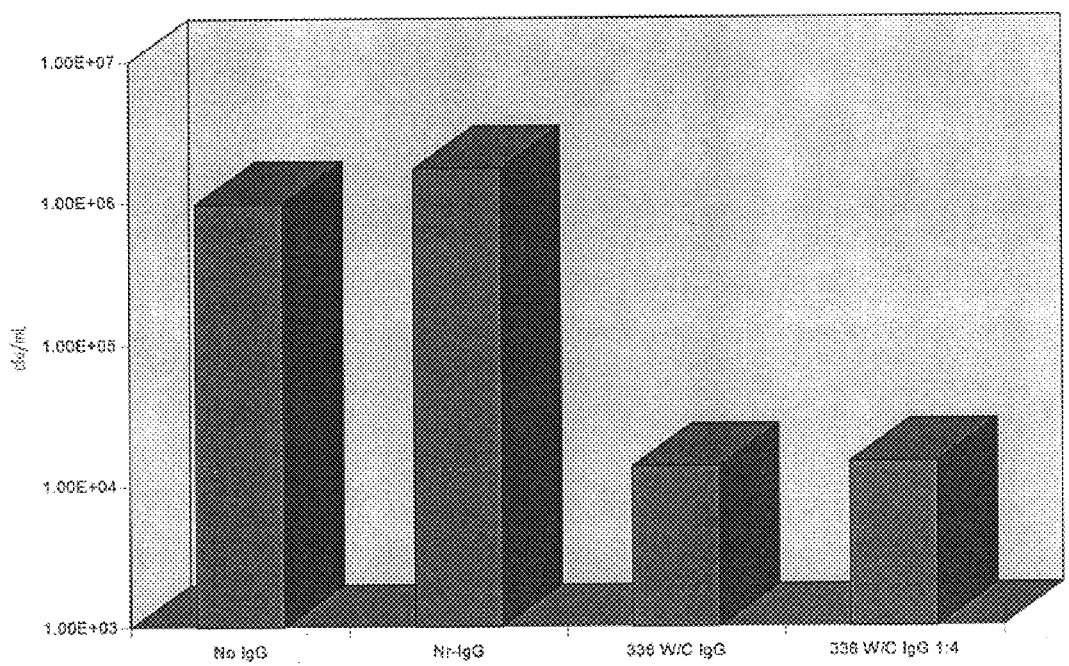

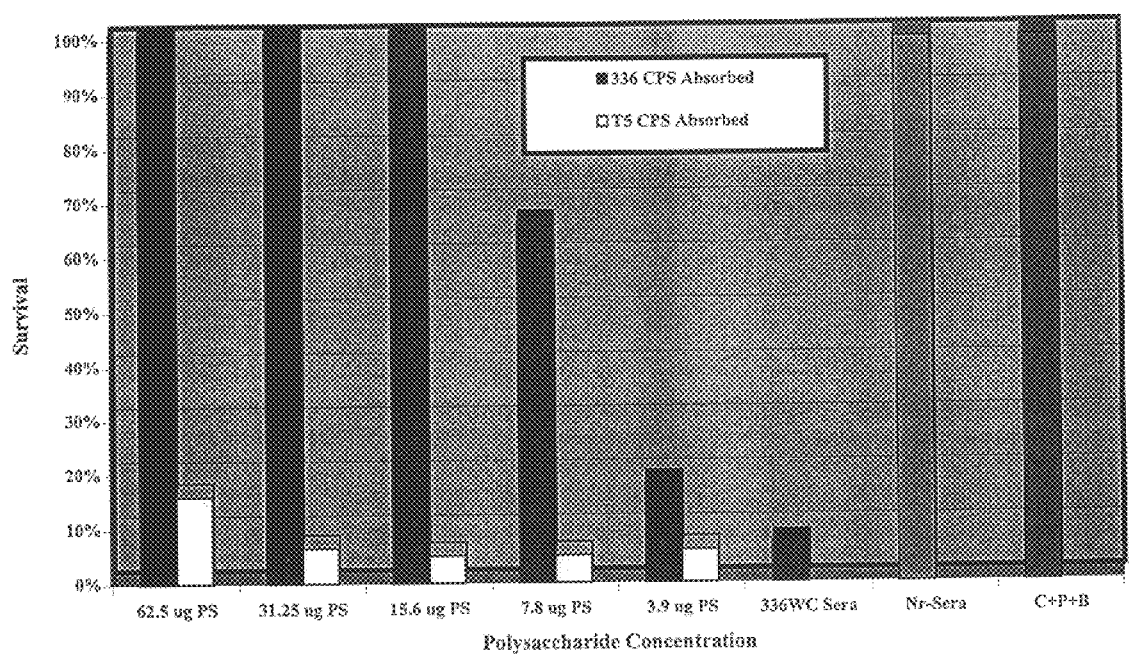
FIG 4. Reduction in Opsonophagocytic Killing of *S. aureus* 336 Strain by Absorption of 336 Whole Cell Derived Hyperimmune Rabbit Sera with 336 PS but not with T5CPS Absorbed Sera.

STAPHYLOCOCCUS AUREUS ANTIGEN-CONTAINING WHOLE CELL VACCINE

CROSS-REFERENCE TO RELATED APPLICATIONS

This application is a continuing application, under 35 U.S.C. §120, of application Ser. No. 09/102,214, filed Jun. 22, 1998, now U.S. Pat. No. 6,194,161, which is a continuation-in-part of and claims priority to application Ser. No. 08/712,438, filed Sep. 11, 1996, now U.S. Pat. No. 5,770,208.

BACKGROUND OF THE INVENTION

The present invention relates to a novel *Staphylococcus aureus* antigen, and to a method for obtaining and using the antigen.

*S. aureus* causes several diseases in animals and in humans by various pathogenic mechanisms. The most frequent and serious of these diseases are bacteremia and its complications in hospitalized patients. In particular, *S. aureus* can cause wound infections and infections associated with catheters and prosthetic devices. Serious infections associated with *S. aureus* bacteremia include osteomyelitis, invasive endocarditis and septicemia. The problem is compounded by multiple antibiotic resistance in hospital strains, which severely limits the choice of therapy. In addition, *S. aureus* is a major cause of mastitis in dairy and beef cattle, where the infection causes a major loss of income.

A *S. aureus* vaccine would provide a solution for the problem of antibiotic resistance. At least eight different serotypes of *S. aureus* have been identified using polyclonal and monoclonal antibodies to capsular polysaccharide (CPS). Karakawa et al., *J. Clin. Microbiol.* 22:445 (1985). The contents of this document and all others listed herein are incorporated herein by reference.

Surveys have shown that approximately 85–90% of human clinical isolates, and a comparable, although somewhat lower percentage of animal clinical isolates, are capsular polysaccharide Type 5 or Type 8. An individual vaccinated with a vaccine containing Type 5 and Type 8 CPS antigens would be protected from infection by 85–90% of clinically-significant *S. aureus* strains, but a significant risk of infection still would exist. A vaccine containing antigens from the other six serotypes theoretically could provide 100% protection, but would require production and purification of six additional components. This would be untenable from a practical standpoint. On the other hand, an antigen common to the isolates not typeable as Type 5 or Type 8 would enable production of a vaccine containing only three antigens.

SUMMARY OF THE INVENTION

It is therefore an object of the present invention to provide a whole cell vaccine of cells that carry an antigen that is common to a large number of clinically-significant *S. aureus* strains, particularly one that is common to strains associated with infections in animals, particularly cattle.

It is a further object of the invention to provide a whole cell vaccine for prevention or treatment of infections in animals, particularly mastitis in cattle.

It is another object of the invention to provide a hyperimmune globulin composition that contains antibodies directed against bacteria that carry an antigen that is common to a large number of clinically-significant *S. aureus* strains, particularly one that is common to strains associated with infections in animals, particularly cattle.

It is yet another object of the invention to provide a hyperimmune globulin composition that is effective in treatment of infections in animals, particularly mastitis.

In accordance with these and other objects according to the invention, there is provided a whole cell vaccine comprising cells from a strain of *Staphylococcus aureus* that carries an antigen that comprises β-linked hexosamine, that contains no O-acetyl groups detectable by nuclear magnetic resonance spectroscopy and that reacts with antibodies to ATCC 55804. Also provided is a composition comprising the whole cell vaccine, and a sterile, pharmaceutically-acceptable carrier therefor. The vaccine can be administered to a human or animal subject to provide protection against *S. aureus* infection. It is particularly useful in preventing mastitis in animals.

An immunotherapeutic agent against *S. aureus* infection, particularly against mastitis in animals, can be prepared by immunizing human or animal subjects with a composition according to the invention, collecting plasma from the immunized subjects, and harvesting a human or veterinary hyperimmune globulin that contains antibodies directed against *S. aureus* from the collected plasma. The hyperimmune globulin contains antibodies directed against the β-linked hexosamine antigen. An immunotherapy method comprises a step of administering this hyperimmune globulin to a human or animal subject, especially an animal with mastitis, to prevent or treat infection.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 2 is a bar graph showing the ability of 336 conjugate IgG to mediate opsonophagocytosis of a representative strain of *S. aureus* that carries the 336 antigen.

FIG. 3 is a bar graph showing the ability of 336 whole cell IgG to mediate opsonophagocytosis of a representative strain of *S. aureus* that carries the 336 antigen.

FIG. 4 is a bar graph showing the effect of absorption with T5 CPS antigen or 336 antigen on the ability of 336 whole cell IgG to mediate opsonophagocytosis of a representative strain of *S. aureus* that carries the 336 antigen.

DESCRIPTION OF PREFERRED EMBODIMENTS

Figure 1A:
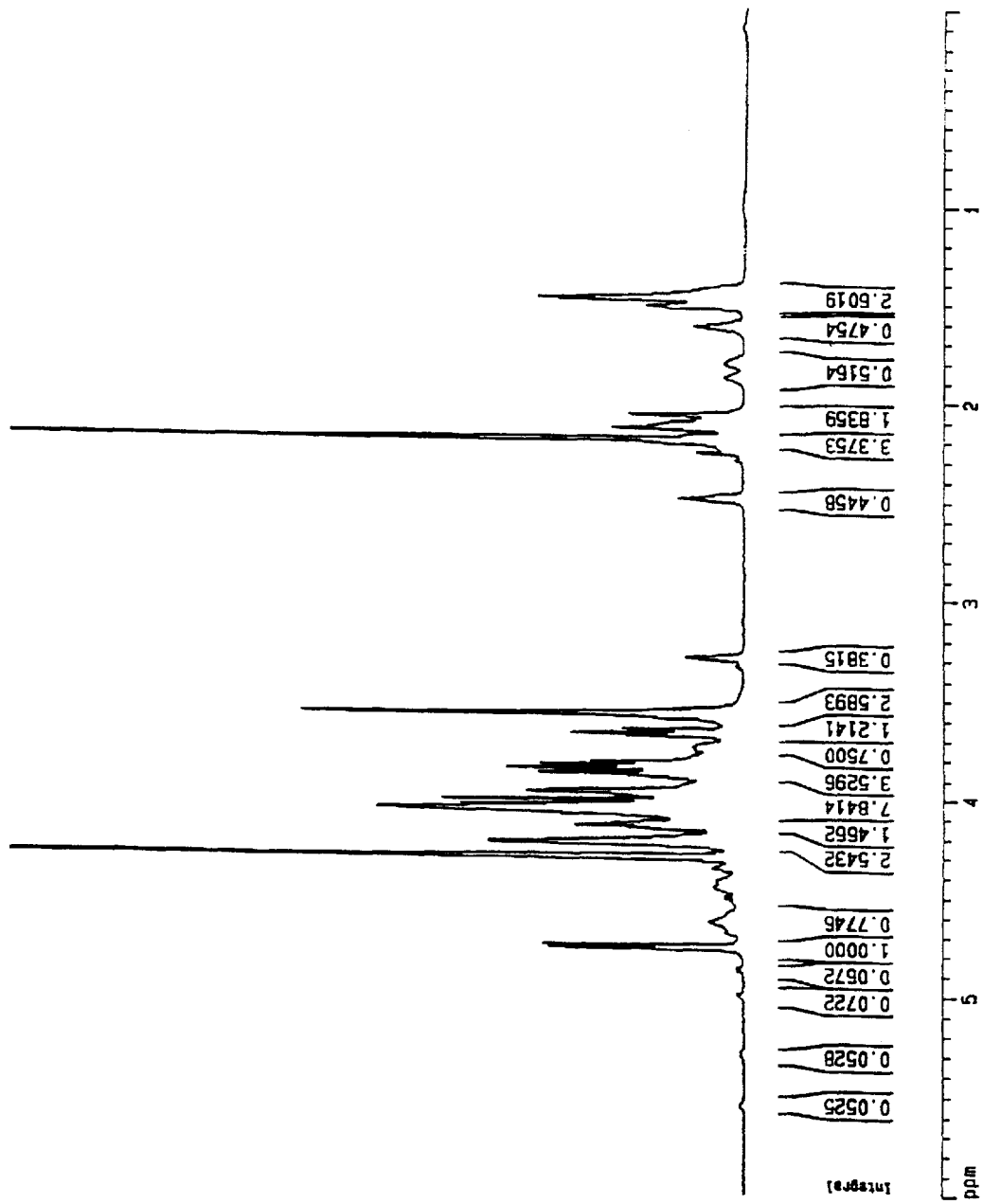
FIGS. 1*a*, 1*b* and 1*c* show the NMR spectra for each of 336, Type 8 and Type 5 *S. aureus* antigens, respectively.

It has been discovered that virtually all strains of *S. aureus* that are not typeable as Type 5 or Type 8 have in common an antigen, here denoted "the 336 antigen." When combined with Type 5 and Type 8 antigens, the 336 antigen represents the basis for a vaccine that provides almost complete protection against infection by clinically significant *S. aureus* isolates. In this regard, a "clinically significant" isolate is an isolate that is pathogenic, in either humans or animals.

More particularly, typing of isolates obtained from various sources has shown that approximately 60% of human isolates are Type 8, approximately 30% are Type 5 and that nearly all of the remaining 10% of isolates are Type 336, as shown in Table 1. Less than 1% of the isolates are not typeable as one of these three types.

TABLE 1

Typing of human clinical isolates

| Source | Total | Type 5 | Type 8 | Type 336* | Not typeable |
|---|---|---|---|---|---|
| Canadian | 350 | 109 (31.5%) | 206 (58.8%) | 34 (9.7%) | 1 (0.3%) |
| Cystic Fibrosis | 147 | 29 (19.7%) | 92 (62.6%) | 19 (12.2%) | — |

*A representative strain of S. aureus that carries the 336 antigen has been deposited under the Budapest Treaty with the American Type Culture Collection, and has been given Accession No. 55804.

Notably, the present inventors obtained 27 human clinical isolates that were not typeable as either Type 5 or Type 8 strains of S. aureus, and that were characterized as being methicillin-resistant strains. All of the 27 strains reacted very strongly with 336 antigen conjugate antibody sera, and thus were typeable as strains that contain 336 antigen.

Typing of bovine mastitis isolates obtained from various sources has shown that approximately 23% of human isolates are Type 8, approximately 22% are Type 5 and that 54% of isolates are Type 336, as shown in Table 2. Thus, 97.5% of isolates that previously were not typeable are typeable as Type 336. Less than 2% of the isolates are not typeable as one of these three types. Therefore, a trivalent whole cell vaccine of Type 5, Type 8 and 336 is particularly indicated for treatment and prevention of veterinary S. aureus infections.

TABLE 2

Typing of bovine mastitis isolates

| Source | Total | Type 5 | Type 8 | Type 336* | Not typeable |
|---|---|---|---|---|---|
| Europe | 102 | 35 (34.3%) | 33 (32.4%) | 29 (28.4%) | 5 (4.9%) |
| United States | 336 | 59 (17.6%) | 68 (20.2%) | 207 (61.6%) | 2 (0.6%) |
| Total | 438 | 94 (21.5%) | 101 (23%) | 236 (53.9%) | 7 (1.6%) |

Antibodies to the 336 antigen do not cross-react with polysaccharides isolated from any of S. aureus Type 5, Type 8, Type 4, K73 (a Type 5 variant strain) or S. epidermidis. The 336 antigen therefore is type-specific, that is, it produces a single band with only the homologous-type antiserum.

The 336 antigen can be obtained in recoverable amount, from certain S. aureus isolates cultured pursuant to the protocols described herein, in substantially pure form. In particular, purified antigen contains less than 1% protein and less than 1% nucleic acids. A "recoverable" amount in this regard means that the isolated amount of the antigen is detectable by a methodology less sensitive than radiolabeling, such as immunoassay, and can be subjected to further manipulations involving transfer of the antigen per se into solution.

To obtain the 336 antigen, a 336 isolate according to the invention first is grown on a Columbia Broth agar plate supplemented with $MgCl_2/CaCl_2$ and then transferred to a 2% NaCl/Columbia starter flask. A 50-liter fermentor that contains the same medium is inoculated with the starter flask. Cells are fermented for 16–24 hours. Following fermentation, cells are killed with 2% final concentration of phenol to ethanol (1:1) and then centrifuged to separate the cells from the supernatant. Antigen is extracted from cell paste. Some 336 antigen is present in the supernatant, but the amount is insignificant as compared to the amount found in the cell paste. Because of the low yield, and the risk of hexose contamination from the media, extraction from supernatant is not preferred.

Enzyme treatments of cell paste with lysostaphin, DNase, RNase and protease, followed by sequential precipitation with 25–75% cold ethanol/$CaCl_2$, results in a crude antigen extraction. The crude material is redissolved in water, dialyzed and lyophilized. The lyophilized material is dissolved in buffer and loaded onto a separatory column equilibrated with the same buffer. The column is washed with 0.15 M NaCl loading buffer and then eluted with a 0.15–0.4 M NaCl gradient. Most of the antigen according to the invention elutes at 0.32 to 0.35 M NaCl. Fractions containing antigen are pooled, dialyzed, concentrated, and lyophilized. The separation can be repeated to obtain better purification. The crude antigen is treated with lysozyme and purified by size on a suitable column and the 336 positive fractions are then pooled, concentrated, dialyzed and lyophilized.

Analysis of purified 336 antigen by gas liquid chromatography (GLC) shows the presence of glucosamine as a major glycosyl component. This is confirmed by sugar analysis on a Dionex system. 1H-NMR spectroscopy of the 336 antigen indicates the presence of β-linked hexosamine as a major carbohydrate component. The antigen additionally comprises a component that is responsible for an observed negative charge displayed by the 336 antigen.

Figure 1B:
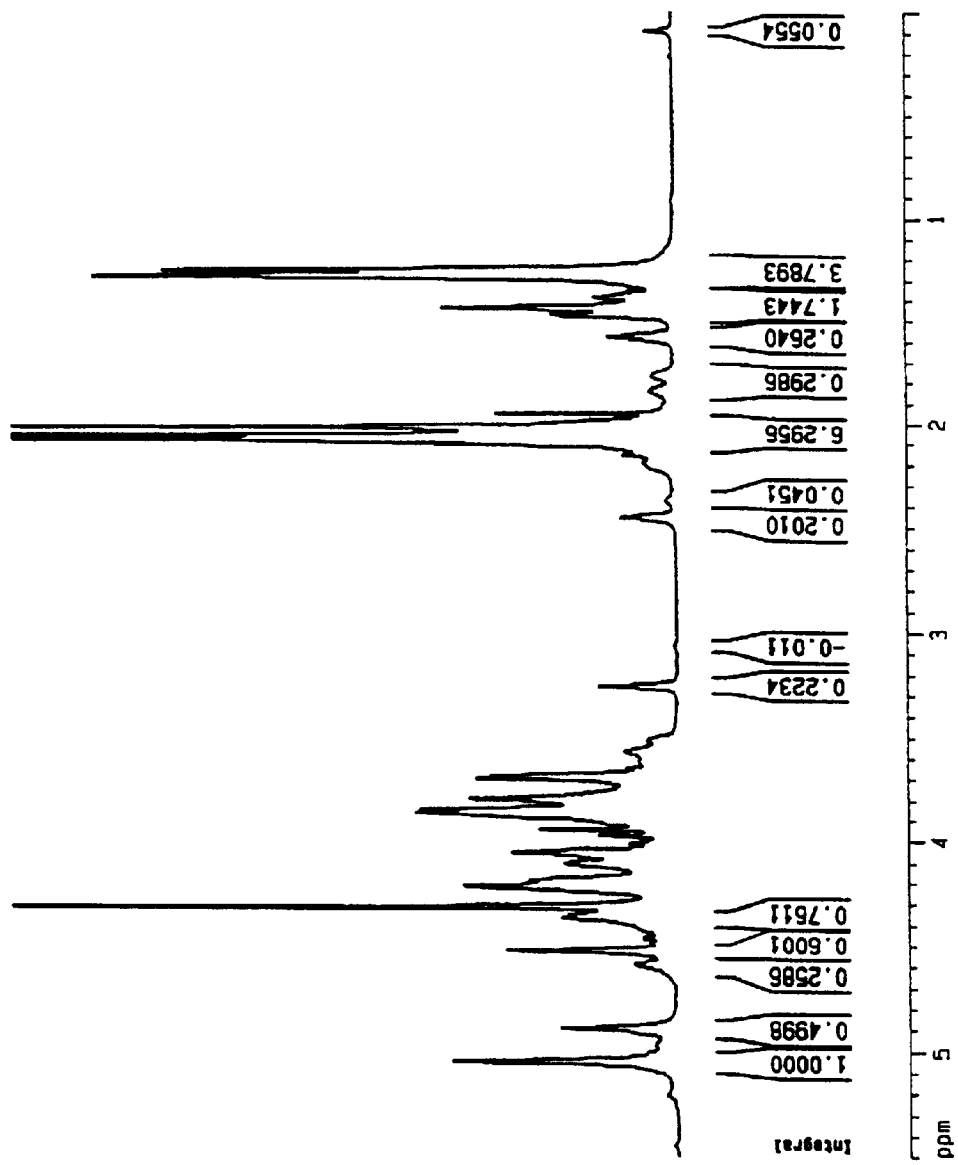
Figure 1C:
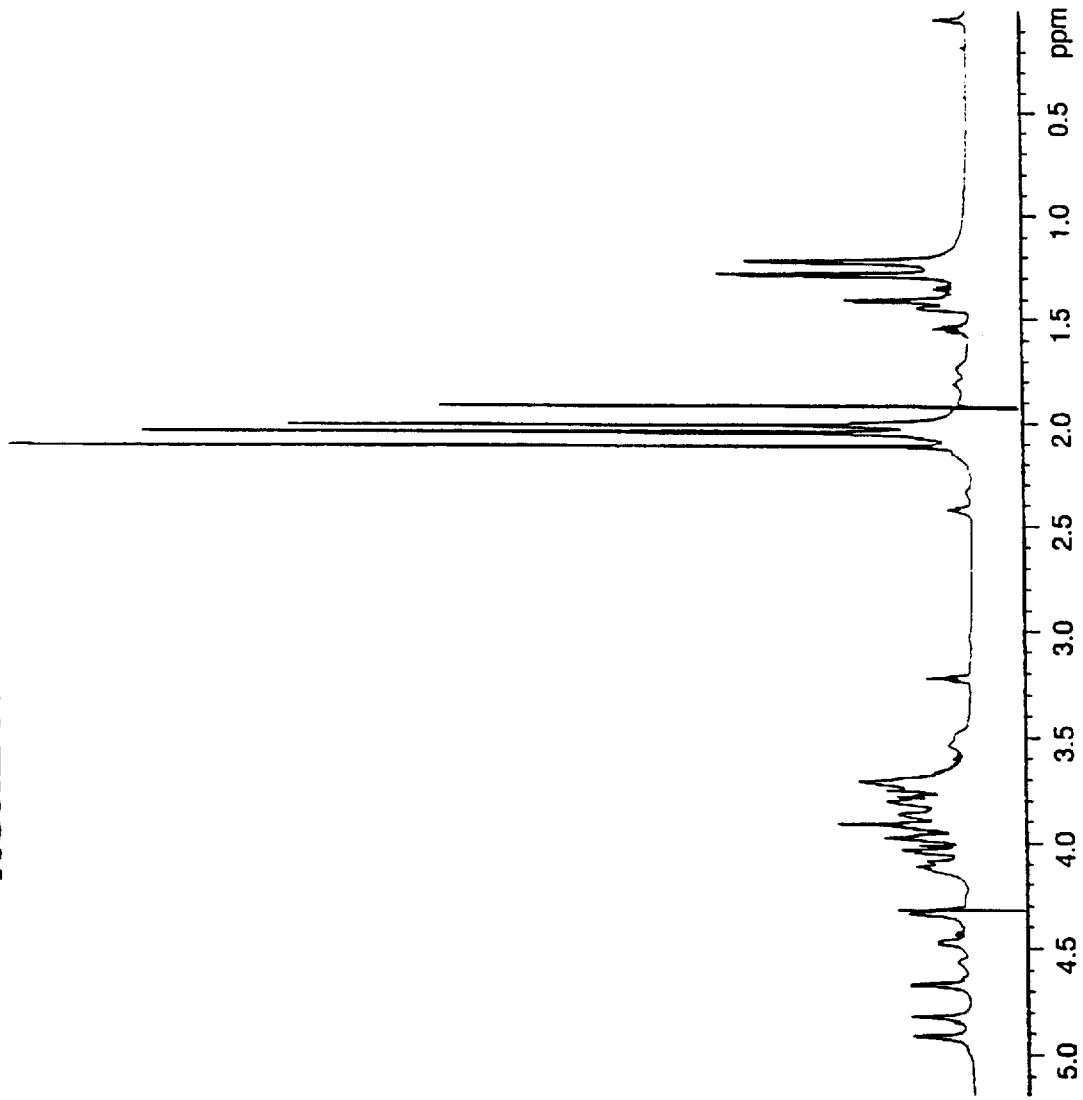

A comparison of the NMR spectra for each of the 336, Type 5 and Type 8 S. aureus antigens, as shown in FIGS. 1a, 1b and 1c, confirms that the 336 antigen is chemically distinct from both the Type 5 and Type 8 S. aureus antigens. The structures of Types 5 and 8 polysaccharide antigens have been elucidated by Moreau et al., Carbohydr. Res. 201:285 (1990); and Fournier et al., Infect. Imm. 45:87 (1984). Both have FucNAcp in their repeat unit as well as ManNAcA which can be used to introduce a sulfhydryl group. The structures are as follows:

Type 5:

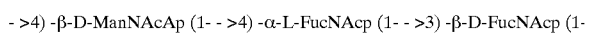

Type 8:

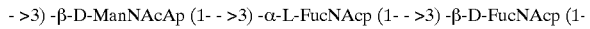

By contrast, the main carbohydrate component of the 336 antigen is β-linked hexosamine.

Induction of bacteremia in laboratory animals requires extremely high numbers of organisms or some previous maneuver to lower the host resistance. In vitro phagocytosis, however, can be studied as a correlate of protective immunity in vivo. In this model, the ability of 336 antigen-specific monoclonal and polyclonal antibodies to opsonize S. aureus in vitro is measured by phagocytosis, according to the method described in Kojima et al., Infect. Dis. Immun. 58:2367–2374 (1990).

Antibodies induced by a 336 antigen vaccine facilitate type-specific phagocytosis. The in vitro phagocytosis assays thus indicate that antibodies to the 336 antigen are protective against infection by *S. aureus* strains that carry the 336 antigen. Vaccines based on Type 5 and Type 8 antigens previously have been shown to be protective against infection by Type 5 and Type 8 strains of *S. aureus*, respectively. Fattom et al. *Inf. and Imm.* 58:2367–2374 (1990) and loc. cit. 64:1659–1665 (1996). A vaccine based on a combination of Type 5, Type 8 and 336 antigen can be used to protect against infection from the majority of clinical *S. aureus* strains.

Preferably, a composition of the 336 antigen or of whole cells containing the 336 antigen according to the present invention "consists essentially of" the 336 antigen, or cells that contain the 336 antigen. In this context, the phrase "consists essentially of" means that the composition does not contain any material that interferes with elicitation of an immune response to the 336 antigen (and to other antigens, if present) when the composition is administered to a subject as a vaccine, or with the antigen-antibody coupling characteristic of a diagnostic assay when the antigen is used in diagnosis. In one embodiment, the composition contains Type 336, Type 5 and Type 8 *S. aureus* antigens.

The antigens according to the invention are useful in the production of diagnostic assays for detecting the presence of *S. aureus* antigen and/or anti-*S. aureus* antibody in a sample. *S. aureus* 336 antigen, or antibody specific to the *S. aureus* antigen, alone or in combination with antigen or antibody to one or both of Type 5 and Type 8 *S. aureus* antigens, is mixed with a sample suspected of containing *S. aureus* antigen or antibody and monitored for antigen-antibody binding. The antigen or antibody is labelled with a radioactive or enzyme label. In a preferred embodiment, antigen or antibody is immobilized on a solid matrix such that the antigen or antibody are accessible to complementary antibody or antigen contacting a surface of the matrix. The sample then is brought into contact with the surface of the matrix, and the surface is monitored for antigen-antibody binding.

For example, the antigen or antibody can be used in an enzyme-linked immunosorbent assay (ELISA), in which antigen or antibody are bound to a solid phase and an enzyme-antibody or enzyme-antigen conjugate is used to detect and/or quantify antibody or antigen present in a sample. Alternatively, a western blot assay can be used in which solubilized and separated antigen(s) is bound to nitrocellulose paper. The antibody then is detected by an enzyme or label-conjugated anti-immunoglobulin (Ig), such as horseradish peroxidase-Ig conjugate by incubating the filter paper in the presence of a precipitable or detectable substrate. Western blot assays have the advantage of not requiring purity greater than 50% for the desired antigen(s). Descriptions of ELISA and western blot techniques are found in Chapters 10 and 11 of Ausubel, et al. (eds.), CURRENT PROTOCOLS IN MOLECULAR BIOLOGY, John Wiley and Sons (1988), the entire contents of which are hereby incorporated by reference.

For use in a vaccine, or in stimulating the synthesis of type 336 specific antibodies in immunized subjects, it is preferable to conjugate the purified 336 antigen to an immunocarrier, usually a polypeptide or protein, to improve the interaction between T and B cells for the induction of an immune response against the antigen. This is particularly important for vaccines intended for use in patients with reduced resistance. An immunocarrier enhances immunogenicity both for active immunization and for preparing high-titered antisera in volunteers for passive immunization. Suitable immunocarriers according to the present invention include tetanus toxoid, diphtheria toxoid, *Pseudomonas aeruginosa* Exotoxin A or its derivatives, recombinantly-produced non-toxic mutant strains of exotoxin A, as described, for example, in Fattom et al., *Inf. and Imm.* 61:1023–1032 (1993), as well as other proteins commonly used as immunocarriers.

Preferably, the antigen or antigen conjugate is administered without an adjuvant in order to avoid adjuvant-induced toxicity. If an adjuvant is used, it is preferred to use one which promotes the protective IgG subtype 2 antibodies. Typical adjuvants include complete Freund's adjuvant (CFA) and incomplete Freund's adjuvant (IFA). Dextran sulfate has been shown to be a potent stimulator of $IgG_2$ antibody against staphylococcal cell surface antigens, and also is suitable as an adjuvant.

The present invention also relates to the use of the 336 antigen to produce polyclonal antibodies or monoclonal antibodies (mouse or human) that bind to or neutralize *S. aureus* strains that carry the 336 antigen. Protocols for producing these antibodies are described in Ausubel, et al. (eds.), *Molecular Cloning: A Laboratory Manual*, Cold Spring Harbor Laboratory, (Cold Spring Harbor, N.Y.)., Chapter 11; in METHODS OF HYBRIDOMA FORMATION 257–271, Bartal & Hirshaut (eds.), Humana Press, Clifton, N.J. (1988); in Vitetta et al., *Immunol. Rev.* 62:159–83 (1982); and in Raso, *Immunol. Rev.* 62:93–117 (1982).

Inoculum for polyclonal antibody production typically is prepared by dispersing the antigen-immunocarrier in a physiologically-tolerable diluent such as saline, to form an aqueous composition. An immunostimulatory amount of inoculum, with or without adjuvant, is administered to a mammal and the inoculated mammal is then maintained for a time period sufficient for the antigen to induce protecting anti-336 antigen antibodies. Boosting doses of the antigen-immunocarrier may be used in individuals that are not already primed to respond to the antigen.

Antibodies can include antibody preparations from a variety of commonly used animals, e.g., goats, primates, donkeys, swine, rabbits, horses, hens, guinea pigs, rats, and mice, and even human antibodies after appropriate selection, fractionation and purification. Animal antisera may also be raised by inoculating the animals with formalin-killed 336 strains of *S. aureus*, by conventional methods, bleeding the animals and recovering serum or plasma for further processing.

The antibodies induced in this fashion can be harvested and isolated to the extent desired by well known techniques, such as by alcohol fractionation and column chromatography, or by immunoaffinity chromatography; that is, by binding antigen to a chromatographic column packing like Sephadex™, passing the antiserum through the column, thereby retaining specific antibodies and separating out other immunoglobulins (IgGs) and contaminants, and then recovering purified antibodies by elution with a chaotropic agent, optionally followed by further purification, for example, by passage through a column of bound blood group antigens or other non-pathogen species. This procedure may be preferred when isolating the desired antibodies from the sera or plasma of humans that have developed an antibody titer against the pathogen in question, thus assuring the retention of antibodies that are capable of binding to the antigen. They can then be used in preparations for passive immunization against 336 strains of *S. aureus*.

A monoclonal antibody composition contains, within detectable limits, only one species of antibody combining site capable of effectively binding to the 336 antigen. Suitable antibodies in monoclonal form can be prepared using conventional hybridoma technology.

To form hybridomas from which a monoclonal antibody composition of the present invention is produced, a myeloma or other self-perpetuating cell line is fused with lymphocytes obtained from peripheral blood, lymph nodes or the spleen of a mammal hyperimmunized with the 336 antigen. It is preferred that the myeloma cell line be from the same species as the lymphocytes. Splenocytes are typically fused with myeloma cells using polyethylene glycol 1500. Fused hybrids are selected by their sensitivity to HAT. Hybridomas secreting the antibody molecules of this invention can be identified using an ELISA.

A Balb/C mouse spleen, human peripheral blood, lymph nodes or splenocytes are the preferred materials for use in preparing murine or human hybridomas. Suitable mouse myelomas for use in the present invention include the hypoxanthine-aminopterin-thymidine-sensitive (HAT) cell lines, a preferred myeloma being P3X63-Ag8.653. The preferred fusion partner for human monoclonal antibody production is SHM-D33, a heteromyeloma available from ATCC, Rockville, Md. under the designation CRL 1668.

A monoclonal antibody composition of the present invention can be produced by initiating a monoclonal hybridoma culture comprising a nutrient medium containing a hybridoma that secretes antibody molecules of the appropriate specificity. The culture is maintained under conditions and for a time period sufficient for the hybridoma to secrete the antibody molecules into the medium. The antibody-containing medium is then collected. The antibody molecules then can be isolated further by well known techniques.

Media useful for the preparation of these compositions are both well known in the art and commercially available, and include synthetic culture media, inbred mice and the like. An exemplary synthetic medium is Dulbecco's Minimal essential medium supplemented with 20% fetal calf serum. An exemplary inbred mouse strain is the Balb/c.

Other methods of preparing monoclonal antibody compositions are also contemplated, such as interspecies fusions, since it is primarily the antigen specificity of the antibodies that affects their utility in the present invention. Human lymphocytes obtained from infected individuals can be fused with a human myeloma cell line to produce hybridomas which can be screened for the production of antibodies that recognize the 336 antigen. More preferable in this regard, however, is a process that does not entail the use of a biological sample from an infected human subject. For example, a subject immunized with a vaccine as described herein can serve as a source for antibodies suitably used in an antibody composition within the present invention.

In a particularly preferred embodiment, monoclonal antibodies are produced to the 336 antigen using methods similar to those described for type-specific antibodies to S. aureus Type 5 and Type 8. The purified monoclonal antibodies are characterized by bacterial agglutination assays using a collection of clinical isolates.

The monoclonal and polyclonal antibody compositions produced according to the present description can be used by passive immunization to induce an immune response for the prevention or treatment of infection by strains of S. aureus that carry the 336 antigen. In this regard, the antibody preparation can be a polyclonal composition. Such a polyclonal composition includes antibodies that bind to the 336 antigen, and additionally may include antibodies that bind to the antigens that characterize Type 5 and Type 8 strains of S. aureus. The polyclonal antibody component can be a polyclonal antiserum, preferably affinity purified, from an animal which has been challenged with the 336 antigen, and preferably also with Type 5 and Type 8 antigens. Alternatively, an "engineered oligoclonal" mixture may be used, which is a mixture of monoclonal antibodies to the 336 antigen, and monoclonal antibodies Type 5 and/or Type 8 antigens.

In both types of mixtures, it can be advantageous to link antibodies together chemically to form a single polyspecific molecule capable of binding to the 336 antigen and one or both of Type 5 and Type 8 antigens. One way of effecting such a linkage is to make bivalent $F(ab')_2$ hybrid fragments by mixing two different $F(ab')_2$ fragments produced, e.g., by pepsin digestion of two different antibodies, reductive cleavage to form a mixture of Fab' fragments, followed by oxidative reformation of the disulfide linkages to produce a mixture of $F(ab')_2$ fragments including hybrid fragments containing a Fab' portion specific to each of the original antigens. Methods of preparing such hybrid antibody fragments are disclosed in Feteanu, LABELED ANTIBODIES IN BIOLOGY AND MEDICINE 321–23, McGraw-Hill Int'l Book Co. (1978); Nisonoff, et al., Arch Biochem. Biophys. 93:470 (1961); and Hammerling, et al., J. Exp. Med. 128:1461 (1968); and in U.S. Pat. No. 4,331,647.

Other methods are known in the art to make bivalent fragments that are entirely heterospecific, e.g., use of bifunctional linkers to join cleaved fragments. Recombinant molecules are known that incorporate the light and heavy chains of an antibody, e.g., according to the method of Boss et al., U.S. Pat. No. 4,816,397. Analogous methods of producing recombinant or synthetic binding molecules having the characteristics of antibodies are included in the present invention. More than two different monospecific antibodies or antibody fragments can be linked using various linkers known in the art.

An antibody component produced in accordance with the present invention can include whole antibodies, antibody fragments, or subfragments. Antibodies can be whole immunoglobulin of any class, e.g., IgG, IgM, IgA, IgD, IgE, chimeric antibodies or hybrid antibodies with dual or multiple antigen or epitope specificities, or fragments, e.g., $F(ab')_2$, Fab', Fab and the like, including hybrid fragments, and additionally includes any immunoglobulin or any natural, synthetic or genetically engineered protein that acts like an antibody by binding to a specific antigen to form a complex. In particular, Fab molecules can be expressed and assembled in a genetically transformed host like E. coli. A lambda vector system is available thus to express a population of Fab's with a potential diversity equal to or exceeding that of subject generating the predecessor antibody. See Huse, W. D., et al., Science 246:1275–81 (1989).

The 336 antigen according to the present invention can be the active ingredient in a composition, further comprising a pharmaceutically acceptable carrier for the active ingredient, which can be used as a vaccine to induce a cellular immune response and/or production in vivo of antibodies which combat S. aureus infection. In this regard, a pharmaceutically acceptable carrier is a material that can be used as a vehicle for administering a medicament because the material is inert or otherwise medically acceptable, as well as compatible with the active agent, in the context of vaccine administration. In addition to a suitable excipient, a pharmaceutically acceptable carrier can contain conventional vaccine additives like diluents, adjuvants, antioxidants, preservatives and solubilizing agents.

In an alternative embodiment, cells that carry the 336 antigen are used in a whole cell vaccine. In this regard, a "whole cell vaccine" includes vaccines made using killed whole bacteria, bacterial lysates or derivatives of whole bacteria. Cells that carry the 336 antigen can be identified and selected for use in the whole cell vaccine by using antibodies to a strain known to carry the 336 antigen, and more preferably by using monoclonal antibodies to isolated antigen as described herein. In this regard, a simple slide agglutination experiment in which antibodies to 336 antigen are mixed with cells can be used.

Deposited strain ATCC 55804 is a representative strain of S. aureus that carries the 336 antigen, and it can be used to produce antibodies useful in identifying other strains that carry the 336 antigen. It is not, however, necessary, to use the deposited strain in order to produce either the whole cell vaccine or antibodies useful in treating or preventing S. aureus infections or in identifying other cells that carry the 336 antigen. ATCC 55804 merely provides one immunologic means of identifying such cells.

As described for purified antigen vaccine above, the whole cell vaccine also comprises a pharmaceutically acceptable carrier. The whole cell vaccine also optionally may contain conventional vaccine additives like diluents, adjuvants, antioxidants, preservatives and solubilizing agents. In a preferred embodiment, the whole cell vaccine contains cells or derivatives of cells which carry the 336 antigen, in addition to cells or derivatives of cells which carry Type 5 and Type 8 antigens.

Vaccines according to the invention can be administered to a subject not already infected with S. aureus, thereby to induce a S. aureus-protective immune response (humoral or cellular), particularly a mastitis-protective response, in that subject. Alternatively, vaccines within the present invention can be administered to a subject in which S. aureus infection already has occurred but is at a sufficiently early stage that the immune response produced to the vaccine effectively inhibits further spread of infection.

In a preferred embodiment, the whole cell vaccine is administered to a female animal to prevent or treat the occurrence of mastitis. In this regard it is administered to female animals considered to be at risk for the development of mastitis, i.e., to animals used in a breeding program, and more particularly to those animals with a prior history of mastitis. The whole cell vaccine is particularly useful in preventing mastitis in a farm animal, such as a cow or a sow, although it also is indicated for use in pet animals, such as dogs and cats.

By another approach, a vaccine of the present invention can be administered to a subject who then acts as a source for immuneglobulin, produced in response to challenge from the specific vaccine ("hyperimmune globulin"), that contains antibodies directed against S. aureus. A subject thus treated would donate plasma from which hyperimmune globulin would then be obtained, via conventional plasma-fractionation methodology, and administered to another subject in order to impart resistance against or to treat S. aureus infection. Hyperimmune globulins according to the invention are particularly useful for immune-compromised individuals, for individuals undergoing invasive procedures or where time does not permit the individual to produce his own antibodies in response to vaccination. Hyperimmune globulins produced to whole cell vaccine are particularly useful in treating S. aureus infections.

Similarly, monoclonal or polyclonal anti-S. aureus antibodies produced according to the present invention can be conjugated to an immunotoxin, and administered to a subject in whom S. aureus infection has already occurred but has not become widely spread. To this end, antibody material produced pursuant to the present description would be administered in a pharmaceutically acceptable carrier, as defined herein.

The present invention is further described by reference to the following, illustrative examples.

EXAMPLES

Example 1

Fermentation of S. aureus

A strain of S. aureus that carries the 336 antigen was cultivated in Columbia broth supplemented with 2% NaCl in an 80-liter fermentor containing 60 liters of broth medium at 370°. The fermentation was started with one liter of a 16 hour old seed culture. The cells were grown with agitation at 200 rpm for 24 hours, to an $A_{650nm}$ of 20.0.

Cells to be used as a vaccine to prepare whole cell antiserum were formalin fixed overnight at room temperature. Cells for purification of antigen were killed by adding phenol-ethanol (1:1, vol/vol) to the fermentor to a final concentration of 2%, and mixing slowly for 2 hours at 15–20° C. No viable cells were detected after this treatment. The cells then were harvested by centrifugation at 14,500×g and stored at −70° C. until use. Approximately 800–900 grams of cell paste (net weight) was obtained from a 60-liter fermentation.

For preparation of cells to be used in preparation of a whole cell vaccine, strains of S. aureus that carry the 336 antigen, the Type 5 antigen and the Type 8 antigen were separately cultivated in Columbia broth supplemented with $MgCl_2/CaCl_2$ at 37° for 18–20 hours, while shaking (200 rpm). The cells were tested by slide agglutination for negative reactivity with S. aureus Wood strain antisera, and then incubated with 3% formalin for 24 hours. The cells were washed 3 times with PBS, typed with S. aureus specific antibodies (T5, T8 or 336) and Wood strain antisera and adjusted to appropriate OD at 540 nm.

Example 2

Preparation of Whole Cell Vaccine and Antiserum

Formalin-fixed cells from Example 1 were adjusted at $OD_{540\ nm}=1$ and combined with physiological saline to produce a vaccine. No adjuvant was used. The vaccine was injected intravenously into rabbits. Rabbits were bled at weekly intervals and positive whole cell serum was collected and pooled. IgG was purified from whole cell serum by a protein G affinity column. The purified material contained 23 mg/ml total IgG (280 UV scan) and substantially less 336 antigen-specific IgG.

Example 3

Purification of 336 Antigen

The cell paste was suspended at 0.5 g (wet weight) per ml in 0.05 M Tris-2 mM $MgSo_4$, pH 7.5. Lysostaphin (100 to 150 μg/ml) was added and incubated at 37° C. for 3 hours with mixing. Thereafter, DNase and Rnase were added to final concentrations of 50 μg/ml each, and the incubation was continued for an additional 4 hours. The reaction mixture was precipitated sequentially with 25 and 75% ethanol in the presence of 10 mM $CaCl_2$.

The 75% ethanol precipitate was pelleted by centrifugation at 12,000×g for 30 minutes, or at a lower rpm for a longer time. The supernatant was transferred to dialysis tubing. The reaction mixture was filtered through a 0.45 μm pore-size membrane and precipitated sequentially with 25 and 75% ethanol in the presence of 10 mM $CaCl_2$. The 75% ethanol precipitate was dialyzed extensively against water at 3 to 8° C. and freeze-dried. The powder was dissolved in 0.2 M NaCl/0.05 M Tris HCl, pH 7.0. The resulting crude material was loaded onto a Q Sepharose column in 0.2 M NaCl/0.05 M Tris HCl, pH 7.0, and eluted with a 0.2–0.4 M NaCl linear gradient. Fractions that contained antigen, as detected by capillary precipitation with antiserum from Example 2, were pooled, dialyzed, and freeze-dried. Most of the antigen eluted at 0.32–0.35 M NaCl/0.05 M Tris HCl.

The crude antigen thus obtained was treated with 1 mg lysozyme per 10 mg crude antigen in 10 mM $CaCl_2$ to digest residual peptidoglycan contamination. The lysozyme-treated crude antigen then was further purified on a Sephacryl S-300 gel filtration column in 0.2 M NaCl/PBS 1× to obtain substantially pure antigen. All reactive material was screened using whole antiserum.

Example 4

Characterization of Antigen

Analysis of purified 336 antigen by gas liquid chromatography (GLC) shows the presence of glucosamine as a major glycosyl component. This is confirmed by sugar analysis on the Dionex system. 1H-NMR spectroscopy of the 336 antigen shows one anomeric proton at 4.751 ppm, corresponding to β-linked hexosamine. In addition, the NMR spectrum shows well separated signals at 4.229 ppm (2H), 3.649 (1H), 3.571 ppm (2H), 2.19 ppm (3H). Signals corresponding to O-acetyl groups are not found. This indicates the absence of O-acetylation, and is clearly distinguished from the 20–80% O-acetylation found on other *S. aureus* type isolates, such as Type 5 and Type 8. The 13C-NMR spectrum shows one signal in the anomeric region at 102.396 ppm. This confirms the presence of monosaccharide as a major component. Other C13-NMR spectrum signals appear at 81.865, 76.641, 74.950, 71.841, 71.051, 70.775, 67.665, 67.142, 61.716, 56.552, 50.355, 43.408 and 23.246 ppm, respectively.

The mobility of purified antigen in immunoelectrophoresis (IEF) indicates the presence of negatively-charged groups. The purified antigen does not contain neutral sugars as detected by the phenol sulfuric assay. The $K_d$ of purified antigen was 0.3 on Superose 12 HR column, which is a smaller molecular size material in comparison with Type 5 ($K_d$ of 0.017), Type 8 ($K_d$ of 0.061) and teichoic acid ($K_d$ of 0.18).

Example 5

Antigen-Immunocarrier Conjugates

Purified antigen was derivatized with 0.5 M adipic acid dihydrazide (ADH) using 100 mm 1-ethyl-3-(3-dimethylaminopropyl)carbodiimide (EDAC) at pH 5.6. Percentage derivatization was achieved in the range of 2 to 7% (w/w). Derivatized purified antigen was conjugated to recombinantly-produced, non-toxic mutant strain of *Pseudomonas aeruginosa* exotoxin A using 50 mM EDAC at 1:1 (antigen:protein), as described in Fattom et al., *Inf. and Imm.* 60:584–589 (1992). The conjugation yield was 50–70%, determined by measurement of protein. The Kd of the conjugate was 0.2 on the Superose 12 HR column.

The conjugate was injected into rabbits with adjuvant (CFA followed by IFA) at a 1:1 ratio. Positive bleeds were combined and IgGs were purified on a protein G column. Conjugate-raised IgG showed identity with antibodies induced by whole cell IgG against the antigen in an immunodiffusion assay. Purified conjugate sera IgG was shown to contain 12.2 mg/ml total IgG by a 280 nm UV scan and 0.7 mg/ml antigen-specific IgG by ELISA. Whole cell serum, whole cell IgG, and conjugate IgG were used in opsonophagocytosis assays and animal models.

Example 6

In vitro Opsonophagocytosis Assays with Antibodies to Antigen/Conjugate Vaccine

Polymorphonuclear leukocytes (PMNs) were obtained from HL-60 cells adjusted to a concentration of $1.0 \times 10^7$ cells per ml in MEM supplemented with 10% fetal bovine serum (FBS). *S. aureus* was grown overnight in Columbia broth supplemented with $MgCl_2/CaCl_2$. The concentration of bacteria was adjusted spectrophotometrically to an OD of 0.02 at 540 nm ($4 \times 10^6$ cells/ml) then adjusted to $1 \times 10^6$ cells/ml in MEM supplemented with 10% FBS. Purified antigen-specific or control non-reactive IgGs were added to facilitate opsonization by PMNs. Baby rabbit complement, diluted 1:8 in MEM supplemented with 10% FBS was used as the negative control.

The reaction mixture contained 25 µl *S. aureus* (concentration $1 \times 10^6$ cells/ml), 25 µl PMNs (concentration $1 \times 10^7$ cells/ml), 25 µl complement, 100 µl sera or antibodies, and sufficient MEM/10% FBS to bring the total reaction volume to 250 µl. At 0 hours, 1 hours and 2 hours, 25 µl of sample were serially diluted. 25 µl of the $10^{-2}$, $10^{-3}$, $10^{-4}$ and $10^{-5}$ dilutions were plated onto TSA agar plates, and incubated overnight at 37° C.

The results are shown in FIG. 2, and show that antibody to conjugate mediates opsonophagocytosis of a representative strain of *S. aureus* that carries the 336 antigen. The results are reported as percent killing by amounts of 336 antigen-specific IgG ranging from 300µg to 128 µg. For comparison, percent killing by an equivalent amount of non-reactive IgG is also reported. PMNs plus complement was used as a control.

Example 7

In vitro Opsonophagocytosis Assays with Antibodies to Whole Cell Vaccine

To evaluate the efficacy of *S. aureus* 336 whole cell vaccine, the *S. aureus* 336 whole cell IgGs were tested for their role to mediate opsonophagocytic killing of *S. aureus* 336 strains in a whole blood opsonophagocytic assay. *S. aureus* 336 cells were grown and adjusted to $2 \times 10^6$ cfu/ml, as described in Example 1. Bacterial suspension (100 µl), saline (100 µl) and antibody solution (100 µl) were added to 700 µl of citrated human blood. After mixing, an aliquot of 25 µl was taken and plated to obtain bacterial counts at time zero. The mixture then was incubated with shaking at 37° C. for one hour and plated. The results are plotted in FIG. 3, and showed a 2 log reduction of colony forming units in the presence of immune IgGs in citrated whole blood, as compared to nonimmune IgGs. Activity of immune IgGs was the same even at a 1:4 dilution, indicating that supplementation of rabbit whole blood with antibodies generated against *S. aureus* 336 isolate produced a strong opsonophagocytic effect against *S. aureus* 336 strains.

Example 8

In vitro Opsonophagocytic Killing Mediated by Whole Cell Hyperimmune Antisera

The importance of *S. aureus* 336 specific antibodies in *S. aureus* 336 whole cell derived hyperimmune rabbit antisera to mediate opsonophagocytic killing of *S. aureus* 336 bacteria was tested by absorption of 336 specific antibodies from *S. aureus* 336 whole cell hyperimmune rabbit antisera with 336 antigen and T5 CPS antigen. Nonimmune rabbit serum was used as a control.

Frozen beads of a *S. aureus* 336 strain (91–14) was inoculated to 5 mL of Columbia $Mg/CaCl_2$ broth and incubated for 16 hours at 37° C. with 200 rpm shaking. For the assay, cells were then adjusted with saline to an approximate concentration of 2×10⁶ CFU/mL (OD$_{540}$=0.02). PMNs (HL-60 cells) were used at concentration 1×10⁷ cells/mL in 1×MEM opsonization media [Minimum Essential Medium, with Earle's salt, without glutamate, GIBCO-BRL], supplemented with 0.1% gelatin [Sigma Chemicals]. Rabbit serum diluted 1:100 with opsonization media was used as a complement source.

Absorption of *S. aureus* 336 whole cell antisera (heat inactivated for 30 minutes at 56° C.) with *S. aureus* 336 antigen and T5 CPS antigen was done as follows. The antigens were dissolved in dH$_2$O at concentrations ranging from 250 ug/mL to 15.6 ug/mL. Antigen solutions (250 uL) with different concentrations of the antigens were mixed with 250 uL of *S. aureus* 336 whole cell antisera diluted to 1:250. The reaction mixture was first incubated for 2 hours at 37° C. and than overnight at 40C. The samples were then centrifuged at 14,000 rpm on an Eppendorf 5415 centrifuge at room temperature. Supernatants were then used in the opsonization assay.

To initiate the assay, 50μl of bacteria, 50μl of diluted complement, 5μl of adjusted HL-60 cells and 50μl of antisera were added per well in polystyrene round bottom micro titer plates (Corning Glass Works). Following mixing, a 25 μl aliquot was taken for determination of Time 0 bacterial counts. The plate was centrifuged for 5 minutes at 1200 rpm at 37° C. and incubated for an hour in 5% CO$_2$ in an incubator. A 25 ul aliquot was taken for determination of CFU/mL of bacteria at one hour ($T_1$).

Bacterial suspensions were diluted 1:10, 1:100, 1:500, 1:1,000 and 1:2,000 in distilled water, and 20 μl of the last four dilutions were plated onto TSA agar plates. Emerging colonies from these plates were used to quantify percent survival by following formulae:

$$\% \text{ kill} = \frac{\text{CFU/mL at } T_1}{\text{CFU/mL at } T_0} \times 100\%$$

The results are summarized in FIG. 4 and show that *S. aureus* 336 hyperimmune sera reduced bacterial growth more then 90%, while nonimmune rabbit antisera did not mediate opsonophagocytic killing as compared to control containing no antisera (complement, PMNs and bacteria, denoted C+P+B). Preincubation of antisera with different amounts of *S. aureus* 336 antigen and T5 CPS antigen showed that opsonophagocytic killing of *S. aureus* 336 whole cell sera is mediated mostly by 336PS specific antibodies. Absorption with T5 CPS antigen did not change the opsonophagocytic killing of 336 whole cell antisera. On the other hand, there is a reduction in opsonophagocytic killing following absorption with 336 antigen, with the degree of reduction correlating to amount of 336 antigen used in the absorption. Inhibition was titered out at low amounts of added 336 antigen. *S. aureus* 336 whole cell immunization did not induce formation of T5 CPS specific or cross-reacting antibodies as shown by the fact that T5 CPS could not absorb the opsonophagocytic killing, even when 62.5 ug of T5 CPS was used for absorption.

What is claimed is:

1. A vaccine that comprises (A) cells, cell lysates, or cell derivatives of *Staphylococcus aureus* which carry an antigen that (a) comprises β-linked hexosamine, (b) contains no O-acetyl groups detectable by nuclear magnetic resonance spectroscopy, and (c) specifically bind with antibodies to *Staphylococcus aureus* Type 336 deposited under ATCC 55804, and a pharmaceutically acceptable carrier.

2. An immunotherapy method comprising administering to a subject an immunostimulatory amount of composition as claimed in claim 1.

3. An immunotherapy method according to claim 2, wherein said subject is a female animal at risk for developing mastitis.

4. An immunotherapy method according to claim 3, wherein said female animal is a cow.

5. An immunotherapy method according to claim 3, wherein said female animal is a sow.

6. An immunotherapy method according to claim 3, wherein said female animal is a cat.

7. An immunotherapy method according to claim 3, wherein said female animal is a dog.

8. An immunotherapy method according to claim 2, wherein said subject is female animal with mastitis.

9. An immunotherapy method according to claim 8, wherein said female animal is a cow.

10. An immunotherapy method according to claim 8, wherein said female animal is a sow.

11. An immunotherapy method according to claim 8, wherein said female animal is a cat.

12. An immunotherapy method according to claim 8, wherein said female animal is a dog.

13. A method of preparing an immunotherapeutic agent against *S. aureus* infection, comprising:
    immunizing subjects with a composition according to claim 1;
    collecting plasma from said immunized subjects; and
    harvesting antibodies directed against *S. aureus* from said collected plasma.

14. An immunotherapeutic agent against *S. aureus* infection, comprising antibodies prepared by the method of claim 13 in a pharmaceutically-acceptable carrier.

15. A vaccine according to claim 1, additionally comprising cells, cell lysates, or cell derivatives of *Staphylococcus aureus* which carry Type 5 antigen, and cells, cell lysates, or cell derivatives of *Staphylococcus aureus* which carry Type 8 antigen.

16. A method of preparing an immunotherapeutic agent against *S. aureus* infection, comprising:
    immunizing subjects with a composition according to claim 15;
    collecting plasma from said immunized subjects; and
    harvesting antibodies directed against *S. aureus* from said collected plasma.

17. A method of preparing a whole cell vaccine according to claim 1, comprising:
    selecting cells of *Staphylococcus aureus* which carry an antigen that (a) comprises β-linked hexosamine, (b) contains no O-acetyl groups detectable by nuclear magnetic resonance spectroscopy, and (c) specifically bind with antibodies to *Staphylococcus aureus* Type 336 deposited under ATCC 55804;
    inactivating said cells; and
    mixing said cells, or lysates or derivatives of said cells, with pharmaceutically acceptable carrier.

18. A vaccine, prepared the method of claim 17.

19. A method of preparing a whole cell vaccine according to claim 17, wherein said cells are selected using antibodies to said antigen.

20. A method of preparing a whole cell vaccine according to claim 19, wherein said antibodies are monoclonal antibodies prepared using isolated antigen.

21. A vaccine, prepared by the method of claim 19.

22. An immunotherapy method comprising administering to subject an immunostimulatory amount of a composition as claimed in claim 19.

23. An immunotherapy method according to claim 22, wherein said subject is a female animal at risk for developing mastitis.

24. An immunotherapy method according to claim 22, wherein said subject is a female animal with mastitis.

25. A method of preparing an immunotherapeutic agent against *S. aureus* infection, comprising:
   immunizing subjects with a composition according to claim 19;
   collecting plasma from said immunized subjects; and
   harvesting antibodies directed *S. aureus* from said collected plasma.

26. An immunotherapeutic agent against *S. aureus* infection comprising antibodies prepared by the method of claim 25 in a pharmaceutically-acceptable carrier.

* * * * *